(12) United States Patent
Wright

(10) Patent No.: US 7,279,031 B1
(45) Date of Patent: Oct. 9, 2007

(54) EMBOLI ELIMINATION APPARATUS

(76) Inventor: David W. Wright, 5 Willowleaf Dr., Littleton, CO (US) 80127

( * ) Notice: Subject to any disclaimer, the term of this patent is extended or adjusted under 35 U.S.C. 154(b) by 438 days.

(21) Appl. No.: 10/998,286

(22) Filed: Nov. 26, 2004

Related U.S. Application Data

(60) Provisional application No. 60/524,824, filed on Nov. 25, 2003.

(51) Int. Cl.
*B01D 19/00* (2006.01)
(52) U.S. Cl. .............................. 96/189; 96/204; 96/220; 96/6; 96/197; 604/126
(58) Field of Classification Search .................. 96/189, 96/204, 206, 220, 6, 197; 95/260, 262, 46, 95/266; 604/126
See application file for complete search history.

(56) References Cited

U.S. PATENT DOCUMENTS

| 4,102,655 | A | * | 7/1978 | Jeffery et al. .................. 96/204 |
| 4,214,883 | A | * | 7/1980 | Raseley et al. ................ 96/189 |
| 4,433,971 | A | * | 2/1984 | Lindsay et al. ............. 604/122 |
| 5,019,141 | A | * | 5/1991 | Granville et al. ............. 96/165 |
| 5,674,199 | A | * | 10/1997 | Brugger ....................... 604/122 |
| 6,746,514 | B2 | * | 6/2004 | Bedingfield et al. ........... 95/46 |

* cited by examiner

*Primary Examiner*—Duane Smith
*Assistant Examiner*—Douglas J. Theisen
(74) *Attorney, Agent, or Firm*—John D. Wright; Dickinson Wright PLLC

(57) ABSTRACT

An apparatus has a body with a wall defining at least in part an enclosed chamber. The wall has a first opening providing fluid flow into the chamber and a second opening providing fluid flow out of the chamber. The wall has a vent allowing gas to pass outwardly from the chamber. An outlet tube extends from the second opening into the chamber and an aperture. The aperture allows fluid within the chamber to enter the outlet tube and flow outwardly from the chamber through the second opening. Bubbles within the chamber are prevented from entering the outlet tube regardless of the orientation of the body.

20 Claims, 7 Drawing Sheets

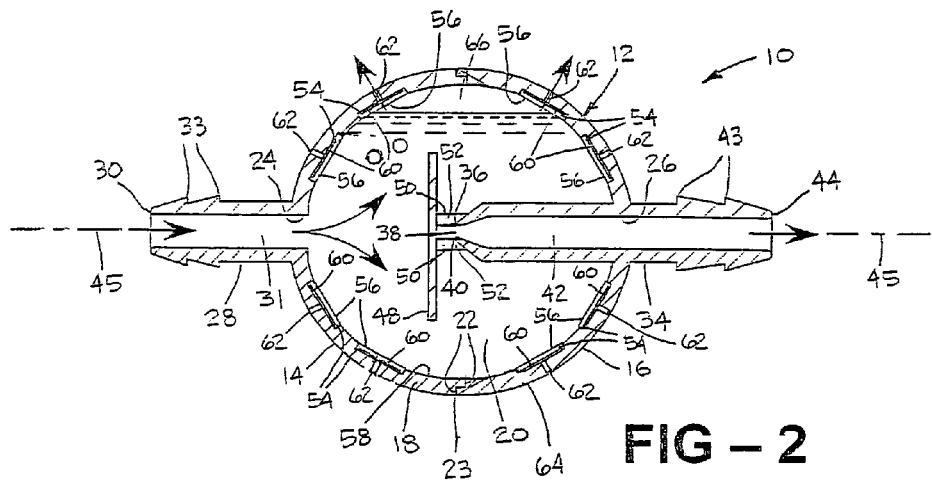

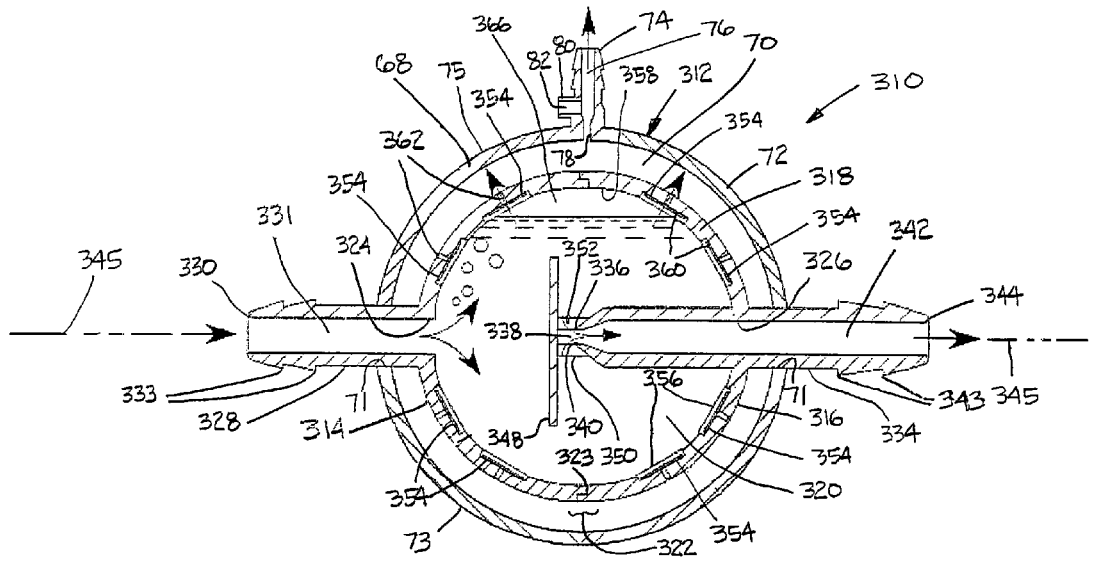
FIG – 11
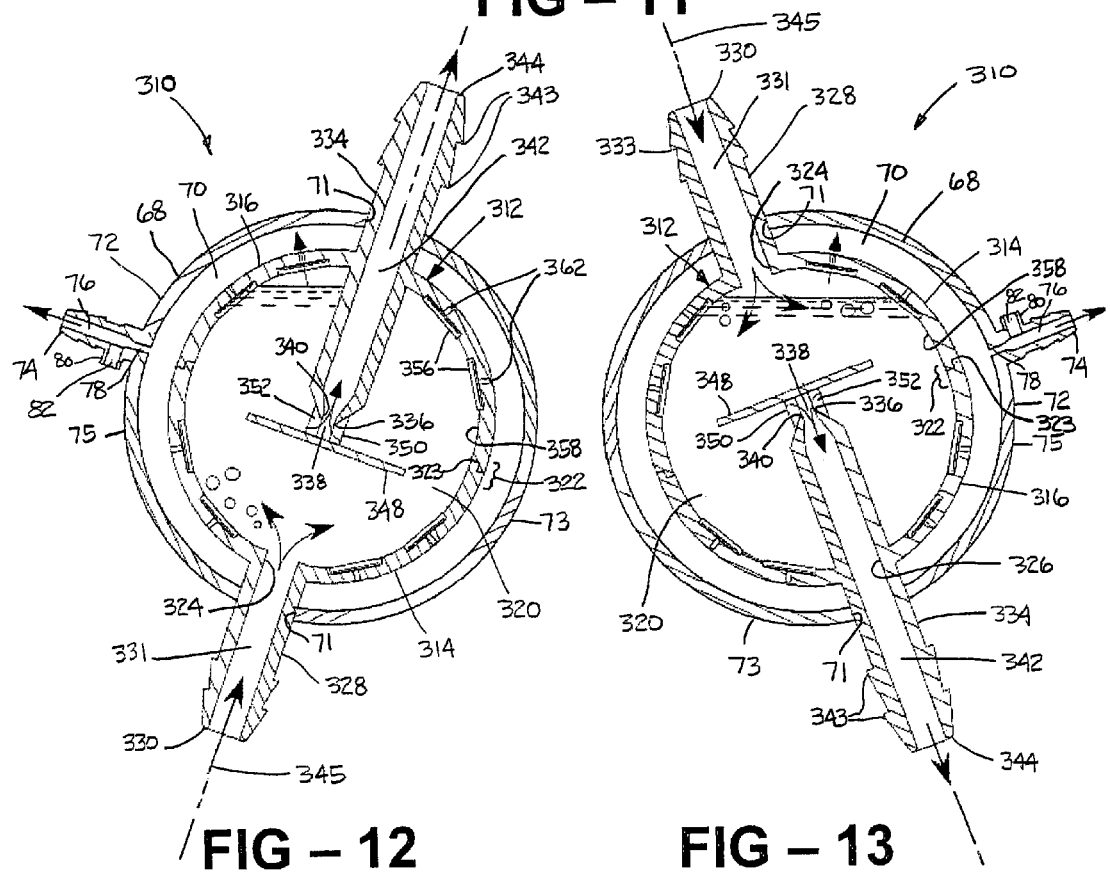
FIG – 12  FIG – 13

FIG – 15  FIG – 16

EMBOLI ELIMINATION APPARATUS

REFERENCE TO CO-PENDING APPLICATION

This application claims the benefit of U.S. Provisional Application No. 60/524,824, filed Nov. 25, 2003.

BACKGROUND OF THE INVENTION

1. Field of the Invention

This invention relates generally to bubble traps for eliminating gas bubbles from a flow of blood or transfusate through a fluid line.

2. Related Art

Conventionally, bubble traps comprise a wall defining a chamber, with an inlet providing fluid flow into the chamber and an outlet providing fluid flow out of the chamber. Generally, the inlet and outlet are separated by an expanded chamber volume to establish a low velocity flow path for the fluid traveling between the inlet and outlet. As the fluid flows from the inlet to the outlet, the bubbles within the volume of fluid generally rise to a gas dome within the chamber to be vented from the chamber. Conventionally, bubble traps must be maintained in a specific orientation to enable the bubble trap to function effectively. Otherwise, if the bubble trap is skewed from its proper orientation, the bubbles within the flow of fluid can not be removed from the flow of fluid, thereby negating the purpose of the bubble trap.

Additionally, bubble traps containing a valve vent must be purged of bubbles periodically by manual or automatic intervention. Some bubble traps contain a gas permeable hydrophobic membrane barrier between an inner surface of the chamber and an exterior ambient environment. In these devices, the pressure within the fluid path is greater than the ambient environment, thus forcing the bubbles through the gas permeable hydrophobic membrane. These devices, though largely effective in their purpose of removing bubbles from the flow of fluid, potentially allow air to ingress into the fluid flow path if the pressure within the chamber is less than the ambient pressure, thereby negatively impacting their intended purpose of removing bubbles from the fluid flow path.

SUMMARY OF THE INVENTION

An apparatus for eliminating bubbles from a flow path of fluid is operable to eliminate the bubbles from the flow of fluid regardless of the orientation of the apparatus and regardless if the pressure within the flow path is less than the ambient atmospheric pressure. The apparatus has a body with a wall defining at least in part an enclosed chamber. The wall has a first opening providing fluid flow into the chamber and a second opening providing fluid flow out of the chamber. The wall has a vent allowing gas to pass outwardly from the chamber. An outlet tube extends from the second opening into the chamber and has an aperture located at a geometric center of the chamber. The aperture allows fluid within the chamber to enter the outlet tube and flow outwardly from the chamber through the second opening. With the chamber having fluid filling greater than half of the volume of the chamber, bubbles within the chamber are prevented from entering the outlet tube regardless of the orientation of the body. Accordingly, the performance of the apparatus is not reliant on remaining in any certain orientation.

Some of the objects, features and advantages of this invention include, by way of example and without limitations, providing an apparatus for removing bubbles from a flow of blood regardless of the orientation of the apparatus, preventing bubbles from entering an outlet flow of blood from the apparatus, reducing the potential sources for bubble entry into the output flow of blood from the apparatus, and is of relatively simple design and economical manufacture and assembly.

BRIEF DESCRIPTION OF THE DRAWINGS

These and other objects, features and advantages of at least some of the presently preferred embodiments of the invention will be apparent from the following detailed description of the presently preferred embodiments and best mode, appended claims and accompanying drawings, in which:

FIG. 2 is a cross sectional view taken generally along line 2-2 of FIG. 1;

FIG. 3 is a view similar to FIG. 2 showing the apparatus in a first tilted orientation;

FIG. 4 is a view similar to FIG. 2 showing the apparatus in a second tilted orientation;

FIG. 11 is a cross sectional view similar to FIG. 2 of a fourth embodiment of an apparatus embodying the present invention;

FIG. 12 is a view similar to FIG. 11 showing the apparatus in a first tilted orientation;

FIG. 13 is a view similar to FIG. 11 showing the apparatus in a second tilted orientation;

FIG. 15 is a view similar to FIG. 14 showing the apparatus in a first tilted orientation;

FIG. 16 is a view similar to FIG. 14 showing the apparatus in a second tilted orientation;

DETAILED DESCRIPTION OF THE PREFERRED EMBODIMENTS

Figure 1:
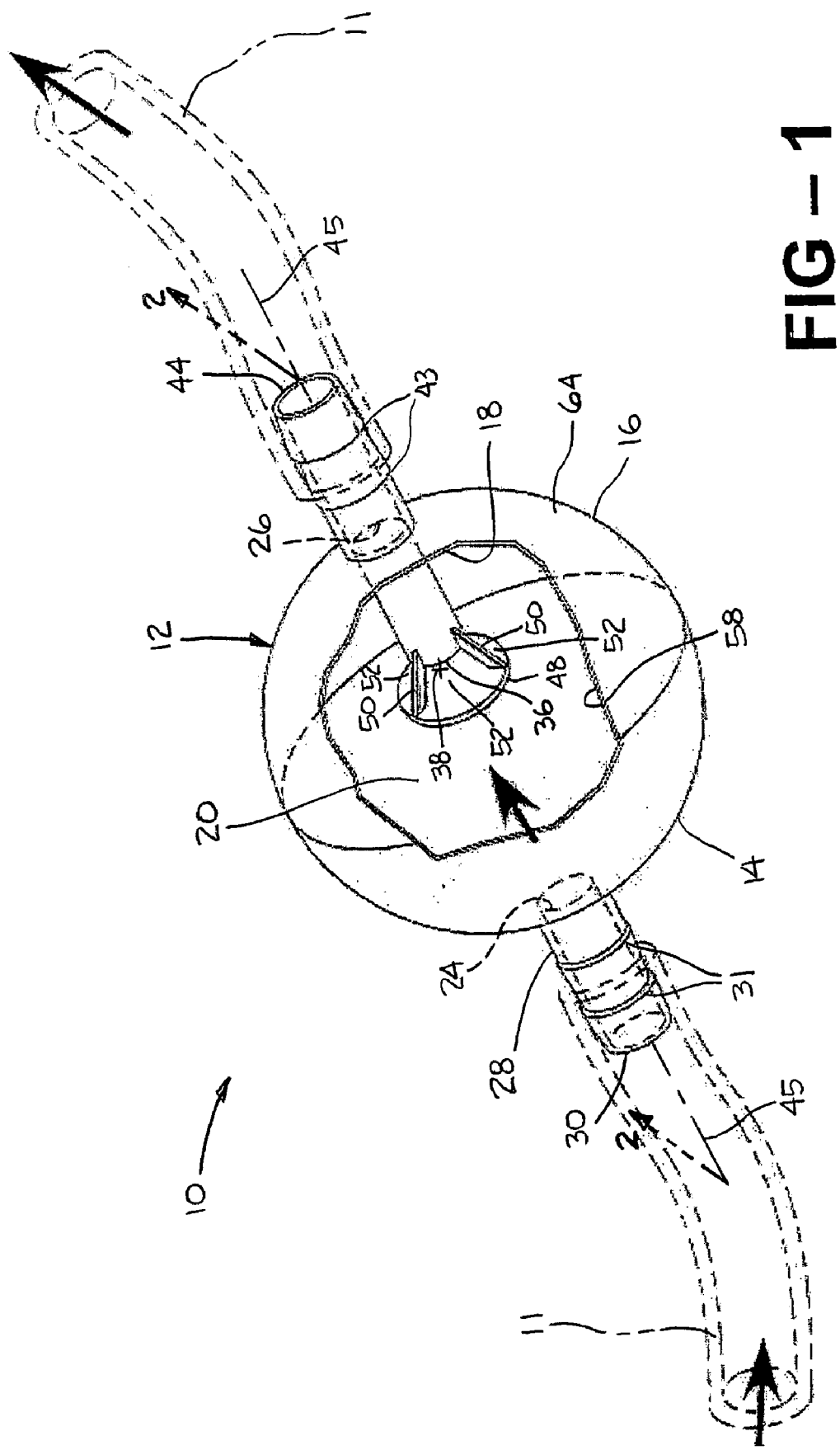
FIG. 1 is a perspective view of one embodiment of an apparatus embodying the present invention shown connected to an input blood line and an output blood line.

Referring in more detail to the drawings, FIG. 1 illustrates an apparatus for eliminating gas, typically in the form of emboli or air bubbles, from a flow of fluid, such as blood or profusion solution, for example, generally at 10. The apparatus 10 is suitable for use in any application requiring the elimination of gas bubbles from fluid, such as, for example, during hemodialysis, a blood transfusion, obtaining a sample of blood, while obtaining blood from a donor, or any other situation requiring the transfer of fluid through a blood or fluid line 11.

The apparatus 10 has a body 12 that is generally spherical in shape and preferably has a pair of mating halves 14, 16, such that when the halves 14, 16 are joined to one another they form a substantially continuous wall 18 defining a chamber 20 therein. Preferably, each half 14, 16 has a stepped perimeter 22 to facilitate mating engagement between the two halves 14, 16 along a joint 23 (FIGS. 2-4). The two halves 14, 16 are preferably fabricated from a polymeric material suitable for sterilization, and are preferably joined to one another using any suitable manufacturing process, such as, for example and without limitation, through the use of RF welding, ultrasonic welding, spin welding, or adhesives such as urethanes, cyanoacrylate, or the like.

Depending on the nature of the application, the chamber 20 may vary in volume. Generally, the chamber 20 is typically believed to have a volume of about 2 ml and accommodating a fluid flow rate of about 0.1 ml/hr-16 ml/min for intravenous uses, and a volume of about 10 ml and accommodating a blood flow rate of about 6 L/min for extracorporeal or bypass applications. Generally, the percent of total volume of the chamber 20 occupied by the gas bubbles within the chamber 20 is believed to be about 25%. Otherwise, it should be recognized that the overall size of the chamber 20 may be varied to accommodate a specific application requirement.

The body 12 of the apparatus 10 has an inlet or first opening 24 extending through the wall 18 of one of the halves 14, and an outlet or second opening 26 extending through the wall 18 of the other half 16. Preferably, an inlet tube 28 is attached to the body 12 and extends from the first opening 24 radially outwardly from the wall 18. The inlet tube 28 terminates in a free end 30 providing a standard connection to the hose or fluid line 11 and has a through passage 31 with a first diameter extending from the free end 30 to the first opening 24. Desirably, the inlet tube 28 has a plurality of inclined steps 33 extending annularly about the inlet tube 28 adjacent the free end 30 to facilitate making a leak proof connection between the inlet tube 28 and the fluid line 11.

The body 12 has an outlet tube 34 connected to the second opening 6 and extending radially inwardly within the chamber 20. The outlet tube 34 terminates at a free end 36 at a geometric center 38 of the chamber 20. The outlet tube 34 has an aperture 40 located at the geometric center 38 allowing blood within the chamber 20 to flow into the outlet tube 34. The outlet tube 34 has a through passage 42 extending from the aperture 40 to another free end 44 of the outlet tube 34. Preferably, as best shown in FIGS. 2-4, the through passage 42 of the outlet tube 34 is axially aligned with the through passage 31 of the inlet tube 28 along an axis 45. The through passage 42 has a second diameter that is, at least in part, less than the first diameter of the inlet tube 28. The second diameter is shown here extending from the free end 36 partially along the length of the outlet tube 34 and flaring radially outwardly until the through passage resumes at about the size of the first diameter of the inlet tube 28. The free end 44 is spaced radially outwardly from the wall 18. Desirably, the outlet tube 34 has a plurality of inclined steps 43 extending annularly about the outlet tube 34 adjacent the free end 44. The inclined steps 43 facilitate making a leak proof connection between the outlet tube 34 and a hose or fluid line.

The apparatus 10 has a baffle wall 48 within the chamber 20 to at least partially obstruct the flow of fluid from flowing directly out of the inlet tube 28 and into the outlet tube 34. Preferably, the baffle wall 48 is connected to the free end 36 by a rib and shown here as a plurality of ribs 50 extending axially away from the free end 36. The ribs 50 are circumferentially spaced from one another to define ports 52 between adjacent ribs 50, wherein the ports 52 provide fluid flow between the ribs 50 into the aperture 40 of the outlet tube 34. The baffle wall 48 is represented as a generally flat piece of planner material spaced from the free end 36, and is preferably formed integrally and as one piece with the ribs 50 and the outlet tube 34. The baffle wall 48 is generally perpendicular to the longitudinal axis 45 of the outlet tube 34 to further prevent any direct flow of fluid from the inlet tube 28 to the outlet tube 34. It should be recognized that other shapes and configurations of the baffle wall 48 are incorporated within the scope of this invention, for example and without limitation, the baffle wall could have a generally dome-shaped or hemispherical shaped surface generally facing the inlet tube 28 to facilitate a laminar flow of the fluid from the inlet tube 28 around the baffle wall 48.

As best shown in FIGS. 2-4, the wall 18 of the body 12 has a plurality of vents 54 distributed over a perimeter of the halves 14, 16. Desirably, the vents 54 are distributed uniformly over the perimeter of the wall 18 to facilitate venting of gas within the chamber 20, regardless of the angular orientation of the apparatus 10. The vents 54 are preferably received in a plurality of pockets 56 within an inner surface 58 of the halves 14, 16 of the wall 18. The pockets 56 have a recessed surface 60 spaced radially outwardly of the inner surface 58, with an orifice 62 extending from each recessed surface 60 through to an outer surface 64 of the halves 14, 16.

The vents 54 are fabricated from a hydrophobic material and are shaped to be received within the pockets 56 to abut the recessed surfaces 60. The vents 54 are preferably heat staked in place, though it should be recognized that any suitable adhesive or heat welding process maybe used to fix the vents 54 within the pockets 56. The hydrophobic vents 54 allow gas within the chamber 20 to pass outwardly from the chamber 20 through the orifices 62, while preventing fluid from passing outwardly of the chamber 20. In addition, the vents 54 act as a one way passage for gas, and thus, act to prevent air from entering the chamber 20 through the orifices 62. With the vents 54 being uniformly distributed about the inner surface 58 of the wall 18, regardless of the orientation of the apparatus 10, a gas dome 66 within the chamber 20 will always be in communication with at least one of the vents 54, thereby enabling the gas to vent outwardly from the chamber 20 under pressure.

To further facilitate venting of the gas bubbles from the chamber 20 through the orifices 62, a back pressure is preferably established within the chamber 20 as a result of the through passage 42 of the outlet tube 34 having, at least in part, a diameter less than the through passage 31 of the inlet tube 28. Accordingly, during a priming stage of the apparatus 10, fluid flows into the chamber 20 until the fluid fills approximately 70-80% of the volume of the chamber 20. Thereafter, the fluid begins to flow outwardly from the chamber 20 through the outlet tube 34. Accordingly, the gas dome 66 is created within the chamber 20 occupying approximately 20-30% of the volume of the chamber 20. Since the inlet tube 28 has a through passage 31 of an increased diameter from that of the outlet tube 34, a positive pressure is established within the chamber 20. The positive pressure results from a back pressure being created at the aperture 40 at the free end 36, located at the geometric center 38 of the chamber 20. Accordingly, the back pressure causes any bubbles within the flow of fluid in the chamber 20 to be driven radially away from the geometric center 38 toward the gas dome 66 in the chamber 20. As best shown in FIGS. 3-4, regardless of the orientation of the apparatus 10, the flow of fluid is free to flow through the inlet tube 28, into the chamber 20 and out the outlet tube 34, while eliminating the bubbles within the volume of fluid through at least one of the vents 54 within the gas dome 66 in the chamber 20.

Figure 5:
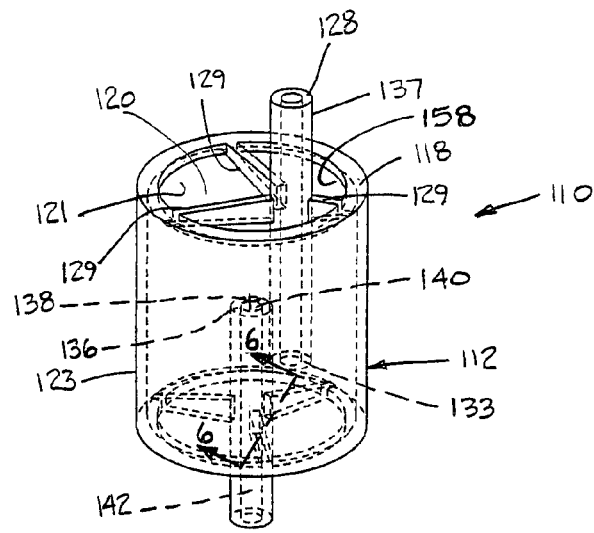
FIG. 5 is a perspective view of a second embodiment of an apparatus embodying the present invention.
Figure 6:
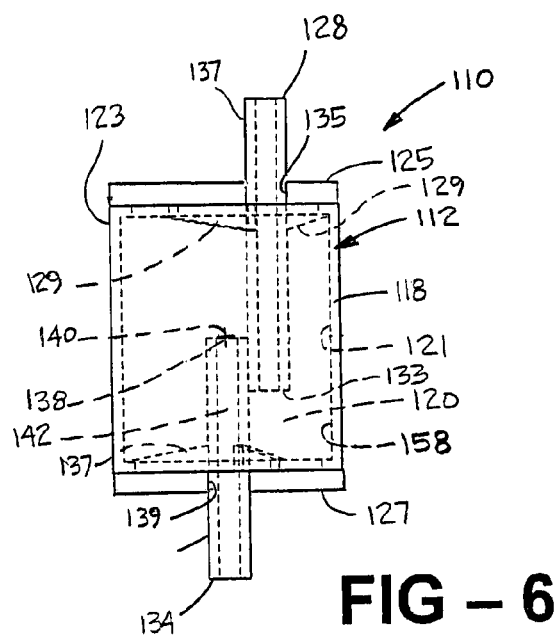
FIG. 6 is a cross sectional view taken generally along line 6-6 of FIG. 5.
Figure 7:
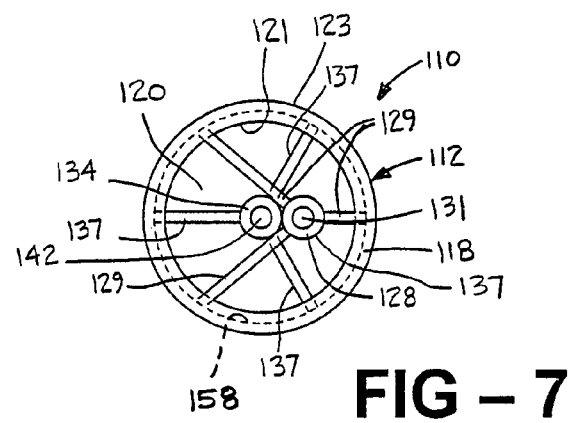
FIG. 7 is a top view of the apparatus of FIG. 5.

Another embodiment of the invention is shown generally at 110 in FIGS. 5-7. Similar reference numerals are used to describe like features of the first embodiment, but are offset by a factor of 100.

The apparatus 110 has a body 112 with a wall 118 defining a chamber 120 therein. The wall 118 is generally cylindrical having an inner surface 121 and an outer surface 123. As shown in FIG. 6, a pair of end caps 125, 127 preferably close off or seal the opposite ends of the cylindrical wall 118.

An inlet tube 128 is preferably supported by a plurality of ribs 129 extending between the inner surface 121 of the wall 118 and an outer surface 137 of the inlet tube 128. The inlet tube 128 is eccentrically positioned relative to the inner surface 121 of the cylindrical wall 118 and extends axially into the chamber 120 beyond a geometric center 138 of the chamber 120 to a free end 133. The inlet tube 128 has a through passage 131 with a first diameter providing for the flow of fluid into the chamber 120. Preferably, the inlet tube 128 extends outwardly from the chamber 120 and away from the end cap 125 to provide a connection to a hose or fluid line as in the previous embodiment. It should be recognized that the end cap 125 has a through hole 135 for receiving the inlet tube 128, and further that the end cap 125 provides an air tight seal around the inlet tube 128 and with the cylindrical wall 118.

The apparatus 110 has an outlet tube 134 preferably supported by a plurality of ribs 141 extending radially inwardly from the inner surface 121 of the wall 118. The outlet tube 134 extends into the chamber 120 to a free end 136. An aperture 140 is formed in the free end 136 providing fluid flow through a through passage 142 of the outlet tube 134. The outlet tube 134 preferably extends outwardly from the chamber 120 through an opening 139 in the end cap 127. It should be recognized that the end cap 127 creates an air tight seal around the outlet tube 134 and with the cylindrical wall 118.

As in the first embodiment, a plurality of vents (not shown) are uniformly distributed around an inner surface 158 of the cylindrical wall 118, and preferably the end caps 125, 127. As in the first embodiment, the vents are hydrophobic, thereby allowing gas to flow outwardly from the chamber 120, while preventing fluid from flowing through the vents, and further preventing gas from entering the chamber 120 through the vents.

As a result of the inlet tube 128 extending past the geometric center 138 of the chamber 120, the fluid flowing into the chamber 120 through the inlet tube 128 is directed initially away from the aperture 140 of the outlet tube 134. Accordingly, the flow of fluid must be redirected in a generally tortuous path before it is able to flow into the aperture 140 and out the outlet tube 134. As in the first embodiment, the outlet tube 134 preferably has a through passage 142 having, at least in part, a second diameter that is less than the diameter of the through passage in the inlet tube 128. Accordingly, as in the first embodiment, a back pressure is established within the chamber 120, thereby facilitating the movement of any air bubbles within the flow of fluid to migrate radially outwardly from the geometric center 138, and ultimately out at least one of the vents within a gas dome (not shown) in the chamber 120. As such, bubbles within the flow of fluid through the chamber 120 are eliminated from the flow of fluid that enters the outlet tube 134. It should be recognized that the inlet tube 128 and the outlet tube 134 may be fabricated integrally and as one piece with the end caps 125, 127, and that mechanisms other than the ribs 129 may be used to support the inlet tube 128 and outlet tube 134 in their respective positions.

Figure 8:
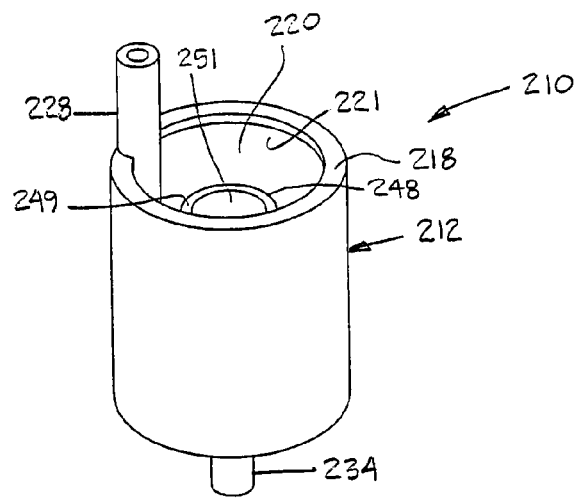
FIG. 8 is a perspective view of a third embodiment of an apparatus embodying the present invention.
Figure 9:
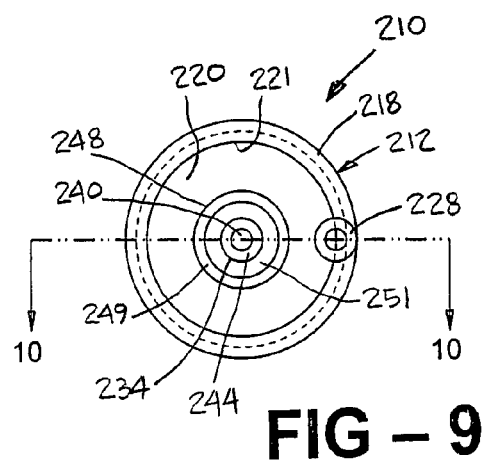
FIG. 9 is a top view of the apparatus of FIG. 8.
Figure 10:
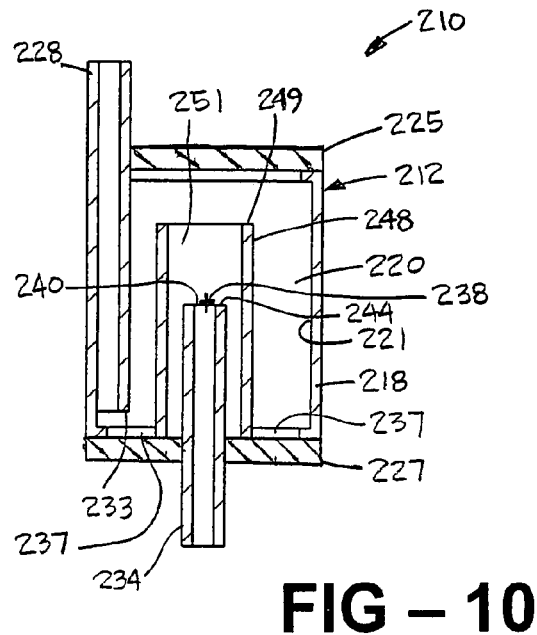
FIG. 10 is a cross sectional view taken generally along the line 10-10 of FIG. 9.

Another embodiment of the invention is shown generally at 210 in FIGS. 8-10. Similar reference numerals are used to describe like features of the first embodiment, but are offset by a factor of 200.

The apparatus 210 has a generally cylindrical body 212 and a pair of end caps 225, 227 (FIG. 10) sealing opposite ends of the body 212. The apparatus 212 has a chamber 220 defined at least in part by an inner surface 221 of a wall 218. The apparatus 210 has an inlet tube 228 preferably constructed integrally and as one piece with the cylindrical wall 218. The inlet tube 228 preferably extends axially outwardly from the end cap 225 to provide a connection to a hose or fluid line, as in the previous embodiments. The inlet tube 228 also extends axially into the chamber 220 beyond a geometric center 238 of the chamber 220 and terminates at an end 233 spaced axially from the end cap 227.

An outlet tube 234 extends axially into the chamber 220 and terminates at a free end 244. An aperture 240 is formed in the free end 244 to allow fluid to flow into the aperture 240 and out the outlet tube 234. As in the previous embodiment, the outlet tube 234 can be supported by a plurality of circumferentially spaced ribs 237 extending radially inwardly from the wall 218. Otherwise, it should be recognized that the outlet tube 234 may be formed integrally with the end cap 227, or formed separately from the end cap 227 and fastened subsequently thereto using any suitable welding process, for example RF welding, spin welding or through the use of an adhesive.

The apparatus 210 has a generally cylindrical baffle wall 248 larger in diameter than the outlet tube 234 arranged generally concentrically to the outlet tube 234 and extending generally from the end cap 227 axially inwardly within the chamber 220. Preferably, the baffle wall 248 extends axially beyond the geometric center 238, and thus axially beyond the free end 244 of the outlet tube 234. The baffle wall 248 terminates at a free end 249 and presents a generally cylindrical passage 251 surrounding the outlet tube 234 within the chamber 220.

The apparatus 210 has a plurality of vents (not shown) uniformly distributed over the inner surface 221 of the wall 218 and preferably in the end caps 225, 227, as in the previous embodiment. As in the previous embodiments, the vents are hydrophobic, thereby allowing gas to flow outwardly from the chamber 220, and further preventing gas from entering the chamber 220 through the vents.

Accordingly, as fluid flows through the inlet tube 228 into the chamber 220, the fluid is redirected through encounter with the end cap 227. The fluid is further redirected for flow by encountering the baffle wall 248 generally surrounding the outlet tube 234. As in the previous embodiments, a back pressure is preferably established by a reduced diameter of the outlet tube passage 240, thereby causing any air bubbles within the fluid flow to be forced radially outwardly from the outlet tube, and in particular radially outwardly from the geometric center 238 of the chamber 220. The air bubbles ultimately rise to a gas dome (not shown) within the chamber 220, and thus outwardly from the chamber 220 through the vents. As in the previous embodiments, the apparatus 210 vents gas from the flow of fluid within the chamber 220 regardless of the orientation of the body 212.

Another embodiment of the invention is shown generally at 310 in FIGS. 11-13. Similar reference numerals are used to describe like features of the first embodiment, but are offset by a factor of 300.

The apparatus 310 has a body 312 that is generally spherical in shape and preferably has a pair of mating halves 314, 316, such that when the halves 314, 316 are joined to one another they form a substantially continuous wall 318 defining a chamber 320 therein. Preferably, each half 314, 316 has a stepped perimeter 322 to facilitate mating engagement between the two halves 314, 316 along a joint 323.

The body 312 of the apparatus 310 has an inlet or first opening 324 extending through the wall 318 of one of the halves 314, and an outlet or second opening 326 extending through the wall 318 of the other half 316. Preferably, an inlet tube 328 is attached to the body 312 and extends from the first opening 324 radially outwardly from the wall 318. The inlet tube 328 terminates in a free end 330 providing a standard connection to a hose or fluid line (not shown) and has a through passage 331 with a first diameter extending from the free end 330 to the first opening 324. Desirably, the inlet tube 328 has a plurality of inclined steps 333 extending annularly about the inlet tube 328 adjacent the free end 330 to facilitate making a leak proof connection between the inlet tube 328 and the fluid line.

The body 312 has an outlet tube 334 connected to the second opening 326 and extending radially inwardly within the chamber 320. The outlet tube 334 terminates at a free end 336 at a geometric center 338 of the chamber 320. The outlet tube 334 has an aperture 340 located at the geometric center 338 allowing fluid within the chamber 320 to flow into the outlet tube 334. The outlet tube 334 has a through passage 342 extending from the aperture 340 to another free end 344 of the outlet tube 334. Preferably, the through passage 342 of the outlet tube 334 is axially aligned with the through passage 331 of the inlet tube 328 along an axis 345. The through passage 342 has a second diameter that is, at least in part, less than the first diameter of the inlet tube 328. The second diameter is shown here extending from the free end 336 partially along the length of the outlet tube 334 and flaring radially outwardly until the through passage resumes at about the size of the first diameter of the inlet tube 328. The free end 344 is spaced radially outwardly from the wall 318. Desirably, the outlet tube 334 has a plurality of inclined steps 343 extending annularly about the outlet tube 334 adjacent the free end 344. The inclined steps 343 facilitate making a leak proof connection between the outlet tube 334 and a hose or fluid line.

The apparatus 310 has a baffle wall 348 within the chamber 320 to at least partially obstruct the flow of fluid from flowing directly out of the inlet tube 328 and into the outlet tube 334. Preferably, the baffle wall 348 is connected to the free end 336 by a rib and shown here as a plurality of ribs 350 extending axially away from the free end 336. The ribs 350 are circumferentially spaced from one another to define ports 352 between adjacent ribs 350, wherein the ports 352 provide fluid flow between the ribs 350 into the aperture 340 of the outlet tube 334. The baffle wall 348 is represented as a generally flat piece of planner material spaced from the free end 336, and is preferably formed integrally and as one piece with the ribs 350 and the outlet tube 334. The baffle wall 348 is generally perpendicular to the longitudinal axis 345 of the outlet tube 334 to further prevent any direct flow of fluid from the inlet tube 328 to the outlet tube 334. It should be recognized that other shapes and configurations of the baffle wall 348 are incorporated within the scope of this invention, for example and without limitation, the baffle wall could have a generally dome-shaped or hemispherical shaped surface generally facing the inlet tube 328 to facilitate a laminar flow of the fluid from the inlet tube 328 around the baffle wall 348.

The wall 318 of the body 312 has a plurality of vents 354 distributed over a perimeter of the halves 314, 316. Desirably, the vents 354 are distributed uniformly over the perimeter of the wall 318 to facilitate venting of gas within the chamber 320, regardless of the angular orientation of the apparatus 310. The vents 354 are preferably received in a plurality of pockets 356 within an inner surface 358 of the halves 314, 316 of the wall 318. The pockets 356 have a recessed surface 360 spaced radially outwardly of the inner surface 358, with an orifice 362 extending from each recessed surface 360 through to an outer surface 364 of the halves 314, 316.

The vents 354 are fabricated from a hydrophobic material and are shaped to be received within the pockets 356 to abut the recessed surfaces 360. The vents 354 are preferably heat staked in place, though it should be recognized that any suitable adhesive or heat welding process maybe used to fix the vents 354 within the pockets 356. The hydrophobic vents 354 allow gas within the chamber 320 to pass outwardly from the chamber 320 through the orifices 362, while preventing fluid from passing outwardly of the chamber 320. In addition, the vents 354 act as a one way passage for gas, and thus, act to prevent air from entering the chamber 320 through the orifices 362. With the vents 354 being uniformly distributed about the inner surface 358 of the wall 318, regardless of the orientation of the apparatus 310, a gas dome 366 within the chamber 320 will always be in communication with at least one of the vents 354, thereby enabling the gas to vent outwardly from the chamber 320 under pressure.

To further facilitate venting of the gas bubbles from the chamber 320 through the orifices 362, a back pressure is preferably established within the chamber 320 as a result of the through passage 342 of the outlet tube 334 having, at least in part, a diameter less than the through passage 331 of the inlet tube 328. Accordingly, during a priming stage of the apparatus 310, fluid flows into the chamber 320 until the fluid fills approximately 70-80% of the volume of the chamber 320. Thereafter, the fluid begins to flow outwardly from the chamber 320 through the outlet tube 334. Accordingly, the gas dome 366 is created within the chamber 320 occupying approximately 20-30% of the volume of the chamber 320. Since the inlet tube 328 has a through passage 331 of an increased diameter from that of the outlet tube 334, a positive pressure is established within the chamber 320. The positive pressure results from a back pressure being created at the aperture 340 at the free end 336, located at the geometric center 338 of the chamber 320. Accordingly, the back pressure causes any bubbles within the flow of fluid in the chamber 320 to be driven radially away from the geometric center 338 toward the gas dome 366 in the chamber 320. As best shown in FIGS. 12-13, regardless of the orientation of the apparatus 310, the flow of fluid is free to flow through the inlet tube 328, into the chamber 320 and out the outlet tube 334, while eliminating the bubbles within the volume of fluid through at least one of the vents 354 within the gas dome 366 in the chamber 320.

To further facilitate the elimination of gas bubbles from the fluid flow path, and particularly from within the chamber 320, another wall, referred to hereafter as the outer wall 68 is constructed radially outwardly, and generally concentrically to the wall, referred to hereafter as the inner wall 318. Accordingly, another chamber 70 is defined between the inner wall 318 and the outer wall 68 to define an air cavity. It should be recognized that openings 71 are provided in the outer wall 68 to form an air tight seal around the inlet tube 328 and the outlet tube 334. The outer wall 68 is formed by joining mating halves 72, 73 in similar fashion as the halves 314, 316 in the previous embodiment.

One of the halves 72 has a vacuum tube 74 extending radially outwardly from an outer surface 75 of the outer wall 68 to provide a vacuum port in the outer wall 68. The vacuum tube 74 has inclined ramps or barbs to facilitate an air tight connection to a vacuum source (not shown). The vacuum tube 74 has a through passage 76 with a necked down section 78 communicating the chamber 70 so that the vacuum source can draw a controlled vacuum pressure with the chamber 70. Further, in addition to the necked down section 78, to regulate the vacuum pressure being drawn in the outer chamber 70, a bleed port 80 has a passage 82 extending generally laterally from the vacuum tube 74. The passage 82 provides flow of atmospheric air through the through passage 76 of the vacuum tube 74 and into the vacuum source, thereby limiting the amount of vacuum pressure capable of being drawn in the outer chamber 70. Generally, a vacuum pressure draw of about 1 mm-150 mm of mercury is established in the outer chamber 70, as necessary.

With a vacuum pressure being drawn through the vacuum tube 74, the pressure in the outer chamber 70 is reassured of being less than the pressure within the inner chamber 320. As such, the relative negative pressure in the outer chamber 70 compared to the pressure in the inner chamber 320 assures that any gas bubbles within the inner chamber 320 will be driven radially outwardly from the geometric center 338 of the inner chamber 320, through the vents 354 and out the orifices 362. Accordingly, any low pressures created within the inner chamber 320, such as may result through the use of peristaltic or roller pumps, and sudden flow rate changes, starting and stopping associated pumps, and siphon pressure downstream of the apparatus 310, for example, are overcome by the relative negative pressure created within the outer chamber 70 in relation to the inner chamber 320.

Figure 14:
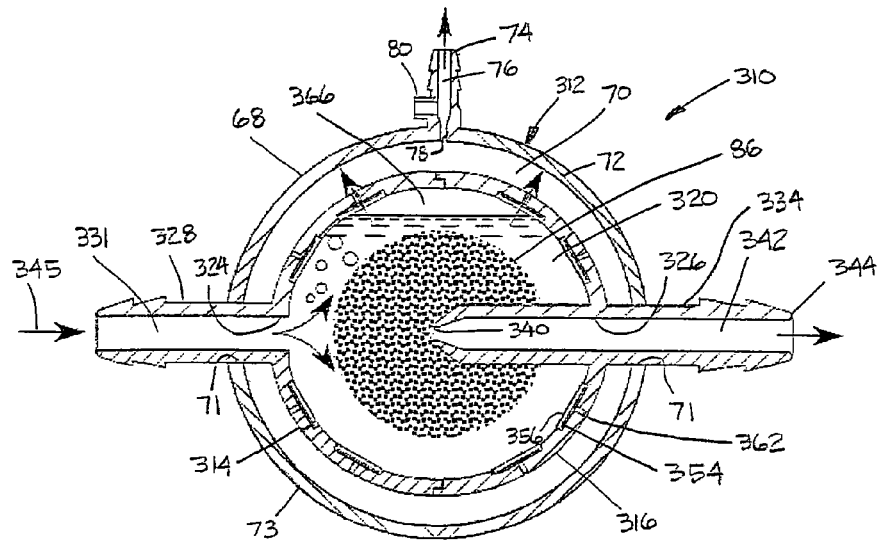
FIG. 14 is a cross sectional view similar to FIG. 2 of a fifth embodiment of an apparatus embodying the present invention.

Another embodiment of the invention is shown generally at 310 in FIGS. 14-16. The same reference numerals as used in the previous embodiment are applicable to represent like features here, while new reference numerals are used to describe a deflector 86 for gas bubbles. Since the overall construction is generally the same as in the previous embodiment, no discussion is provided for the same features hereafter.

The deflector 86 is generally constructed from an open cell material, for example and without limitation, open cell foams, heat sintered materials, porous rigid materials, carbon filters, and other generally inert porous materials, to prevent the passage of gas bubbles through the deflector 86 and into the outlet tube 334. The porosity of the material is sized to prevent gas bubbles from passing through the deflector 86, while at the same time allowing fluid to pass therethrough. Accordingly, as gas bubbles come into contact with the deflector 86, the gas bubbles maintained outside the deflector 86, and generally are driven radially outwardly from the deflector 86 toward the vents 354.

The deflector 86 is attached or bonded generally around the outlet tube 334 to restrict the passage into the aperture 340 to fluid, while preventing gas bubbles from entering the aperture 340. The deflector 86 can be attached to the outlet tube 334 through, for example, a spin welding, hot melt, solvent bond, adhesive layer, or other suitable mechanism.

Figure 17:
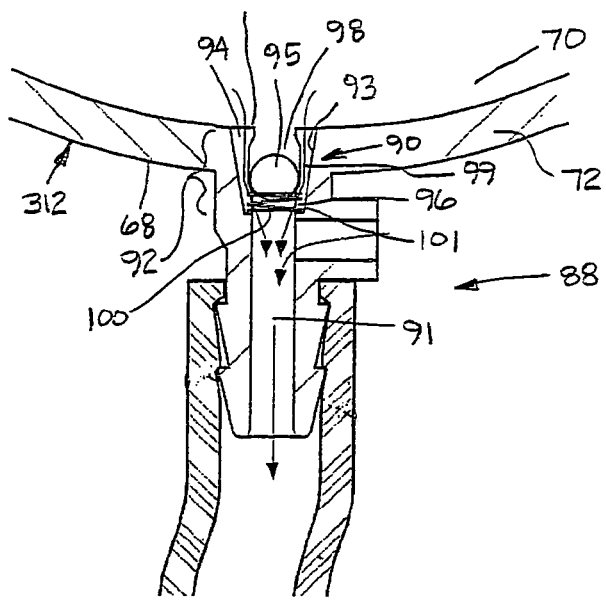
FIG. 17 is a cross sectional view of an alternate construction of a vacuum port shown in a minimum flow position.
Figure 18:
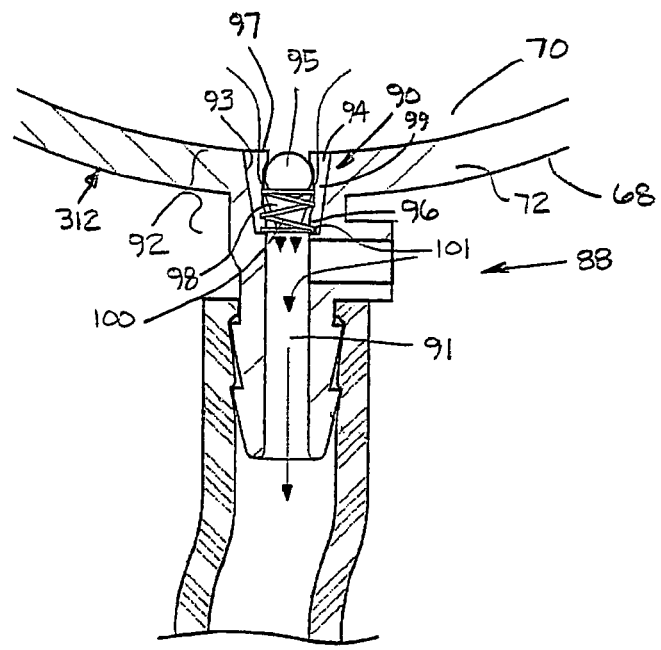
FIG. 18 is a view similar to FIG. 14 showing the vacuum port in a maximum flow position.

Another embodiment of a vacuum tube is shown generally at 88 in FIGS. 17 and 18. Instead of having a necked down section to facilitate regulating the amount of vacuum pressure drawn the outer chamber, as discussed in previous embodiments, the vacuum tube 88 has a check valve 90 operable between a minimum vacuum pressure draw position (FIG. 17) and a maximum vacuum pressure draw position (FIG. 18).

The vacuum tube 88 has a through passage 91 with a generally frustroconical section 92 adjacent an end of the through passage 91 in communication with the outer chamber 70. The frustroconical section 92 has a surface 93 with longitudinally traversing ribs 94 extending radially inwardly therefrom to define a cavity 98 sized to receive a ball valve 95 for movement therein. The ribs 94 have opposite ends 96, 97 that extend radially inwardly beyond a diameter of the ball valve 95 to retain the ball valve 95 within the cavity 98, and have a midsection defining a portion of the cavity 98 having a diameter greater than the ball valve 95. It should be understood that the adjacent ribs 94 define spaces 99 therebetween to allow gas to flow around the ball valve 95 in operation. Accordingly, when the ball valve 95 moves radially outwardly within the cavity 98, the area for gas flow around the ball valve 95 is minimized between the ribs 94 as a result of the ball valve 95 moving into a reduced area of the frustroconical section 92, thereby minimizing the vacuum draw generated by the vacuum source in the outer chamber 70. Otherwise, when the ball valve 95 moves radially inwardly within the cavity 98, the area for gas flow around the ball valve 95 is maximized between the ribs 94 as a result of the ball valve 95 moving into an expanded area of the frustroconical section 92, thereby maximizing the vacuum draw generated by the vacuum source in the outer chamber 70.

Desirably, a spring member 100 abuts a counterbore surface 101 of the frustroconical section 92 and engages the ball valve 95 to bias the ball valve 95 toward the maximum vacuum pressure position. Accordingly, a maximum vacuum pressure is drawn by the vacuum source as needed, until a backpressure is sufficiently strong enough to overcome the biasing force of the spring member 100. It should be understood that as the back pressure increases in the inner chamber 320, the necessity for a vacuum pressure draw within the outer chamber 70 generally decreases.

The disclosed embodiments are representative of presently preferred constructions of the invention, but are intended to be illustrative rather than definitive thereof. One ordinarily skilled in the art will recognize other embodiments upon viewing this disclosure in its entirety. It should be understood that other embodiments of the invention which accomplish the same or similar function are incorporated herein. The invention is defined by the following claims.

I claim:

1. An apparatus for eliminating bubbles from a flow path of fluid, comprising:
   a body having a wall defining at least in part a substantially enclosed chamber with a defined volume, said wall having a first opening providing fluid flow into said chamber and a second opening providing fluid flow out of said chamber, said wall having a vent allowing gas to pass outwardly from said chamber; and
   an outlet tube extending from said second opening into said chamber, said outlet tube having an aperture located at a geometric center of said chamber allowing fluid within said chamber to enter said outlet tube and flow outwardly from said chamber through said second opening and inhibiting bubbles contained within said volume of said chamber from entering said outlet tube regardless of the orientation of said body when said chamber is filled with fluid exceeding half of said volume of said chamber.

2. The apparatus of claim 1 wherein said vent is constructed of a one way hydrophobic material preventing gas from entering said chamber through said vent and preventing fluid from passing outwardly from said chamber through said vent.

3. The apparatus of claim 1 wherein said body is substantially spherical.

4. The apparatus of claim 1 wherein said outlet tube terminates at a free end at said geometric center of said chamber.

5. The apparatus of claim 4 further comprising a baffle wall spaced from said free end and at least partially obstructing the flow of fluid into said aperture of said outlet tube.

6. The apparatus of claim 5 wherein said baffle wall is connected to said free end by a rib extending axially away from said free end of said outlet tube.

7. The apparatus of claim 6 wherein said rib comprises a plurality of circumferentially spaced ribs extending away from said free end and attached to said baffle wall, said ribs defining ports between adjacent ribs to provide fluid flow between said ribs into said aperture of said tube.

8. The apparatus of claim 5 wherein said tube has a longitudinal axis and said baffle wall is generally perpendicular to said axis.

9. The apparatus of claim 1 further comprising an inlet tube attached to said body providing fluid flow into said chamber through said first opening, said inlet tube being separate and spaced from said outlet tube.

10. The apparatus of claim 9 wherein said inlet tube extends into said chamber past said geometric center of said chamber.

11. The apparatus of claim 10 wherein said inlet tube and said outlet tube are axially misaligned with one another.

12. The apparatus of claim 11 further comprising a substantially cylindrical baffle wall extending around said outlet tube.

13. The apparatus of claim 12 wherein said baffle wall is concentric with said outlet tube.

14. The apparatus of claim 1 further comprising an inlet tube attached to said wall, said inlet tube having a through passage with a first diameter, said outlet tube having a through passage with a second diameter, and said second diameter being less than said first diameter.

15. An apparatus for eliminating bubbles from a flow path of fluid, comprising:
an inner wall defining at least in part a substantially enclosed chamber, said wall having a first opening providing fluid flow into said chamber and a second opening providing fluid flow out of said chamber, said inner wall having a vent allowing gas to pass outwardly from said chamber;
an outer wall spaced radially outwardly from said inner wall defining a cavity between said inner and outer walls, said vent communicating said chamber with said cavity for the flow of gas into said cavity; and
an outlet tube extending through said outer wall and through said second opening in said inner wall to allow fluid within said chamber to flow out of said chamber through said outlet tube.

16. The apparatus of clam 15 wherein said outlet tube has an aperture located at a geometric center of said chamber.

17. The apparatus of claim 15 further comprising a vacuum port in said outer wall adapted for operable connection with a vacuum source, said chamber having one pressure defined therein, said cavity having another pressure defined therein resulting at least in part from a vacuum drawn through said vacuum port, said another pressure in said cavity being less than said one pressure in said chamber.

18. The apparatus of claim 17 wherein said vacuum port is defined in part by a vacuum tube, said vacuum tube having a check valve to regulate amount of vacuum established within said cavity.

19. The apparatus of claim 15 further comprising an inlet tube in fluid communication with said chamber, said inlet tube having a through passage with a first diameter, said outlet tube having a through passage with a second diameter, and said second diameter being less than said first diameter.

20. The apparatus of claim 15 further comprising a deflector attached to the outlet tube within the chamber to prevent gas bubbles from entering the outlet tube.

* * * * *